(12) United States Patent
Sun et al.

(10) Patent No.: US 6,522,137 B1
(45) Date of Patent: Feb. 18, 2003

(54) TWO-DIMENSIONAL MAGNETIC RESONANCE IMAGING IN A BOREHOLE

(75) Inventors: Boqin Sun, Sugar Land, TX (US); Reza Taherian, Stafford, TX (US); Abdurrahman Sezginer, Houston, TX (US); Steven F. Crary, Sugar Land, TX (US)

(73) Assignee: Schlumberger Technology Corporation, Houston, TX (US)

( * ) Notice: Subject to any disclaimer, the term of this patent is extended or adjusted under 35 U.S.C. 154(b) by 138 days.

(21) Appl. No.: 09/605,805

(22) Filed: Jun. 28, 2000

(51) Int. Cl.$^7$ .................................................. G01V 3/00
(52) U.S. Cl. ...................................................... 324/303
(58) Field of Search ................................ 324/303, 309, 324/300, 306; 175/45

(56) References Cited

U.S. PATENT DOCUMENTS

| | | | |
|---|---|---|---|
| 4,684,891 A | * 8/1987 | Feinberg | 324/309 |
| 5,280,243 A | 1/1994 | Miller | |
| 5,428,291 A | * 6/1995 | Thomann et al. | 324/303 |
| 5,757,186 A | 5/1998 | Taicher et al. | |
| 6,111,408 A | * 8/2000 | Blades et al. | 324/303 |
| 6,173,793 B1 | * 1/2001 | Thompson et al. | 175/45 |

FOREIGN PATENT DOCUMENTS

| | | |
|---|---|---|
| EP | 0 581 666 A2 | 2/1994 |
| EP | 0 581 666 A3 | 8/1994 |
| GB | 2 279 754 | 1/1995 |
| GB | 2 339 024 | 1/2000 |
| GB | 2 342 170 | 4/2000 |
| WO | WO 99/36801 | 7/1999 |

OTHER PUBLICATIONS

J Tabary, M Fleury, M Locatelli & JP Martin, "A High Resolution NMR Logging Tool: Concept Validation," *SPWLA* 41$^{st}$ Annual Logging Symposium, Jun. 4–7, 2000, pp. 1–14.

DK Sodickson & WJ Manning, "Simultaneous Acquisition of Spatial Harmonics (SMASH): Fast Imaging with Radiofrequency Coil Arrays," Beth Israel Deaconess Medical Center and Harvard Medical School, Boston MA (Williams & Wilkins 1997).

\* cited by examiner

Primary Examiner—Edward Lefkowitz
Assistant Examiner—Tiffany A. Fetzner
(74) Attorney, Agent, or Firm—Kevin P. McEnaney; Brigitte L. Jeffery; John J. Ryberg

(57) ABSTRACT

A downhole NMR measurement apparatus for use in a borehole includes at least one magnet, at least one RF transmission coil, at least one gradient coil and circuitry. The magnet(s) establish a magnetic field in a region of a formation that at least partially surrounds the measurement apparatus. The RF transmission coils(s) transmit RF pulses pursuant to an NMR pulse sequence into the region to, in combination with the magnetic field, induce the generation of spin echo signals from a resonance volume within the region. The gradient coil(s) establish a pulsed gradient field in the resonance volume, and the circuitry is coupled to the gradient coil(s) to control the generation of the pulsed gradient field to phase encode the spin echo signals for purposes of high resolution imaging of the formation.

43 Claims, 11 Drawing Sheets

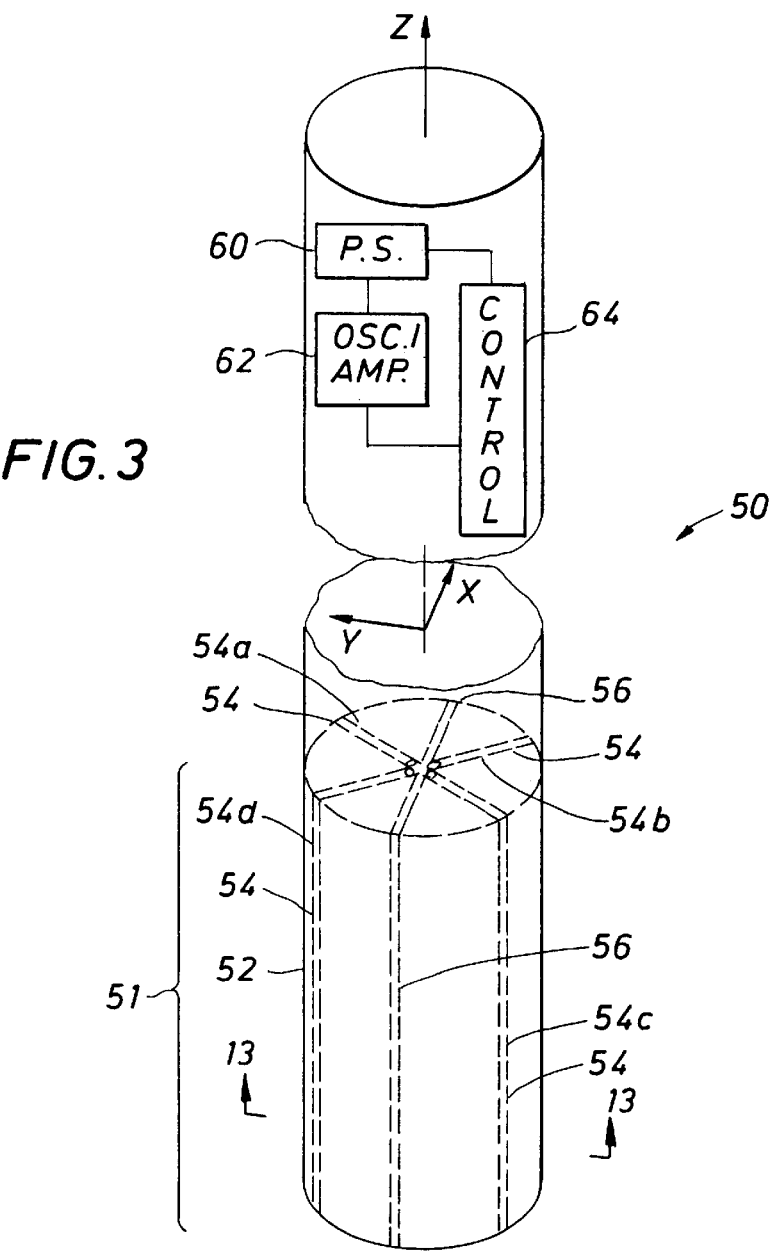
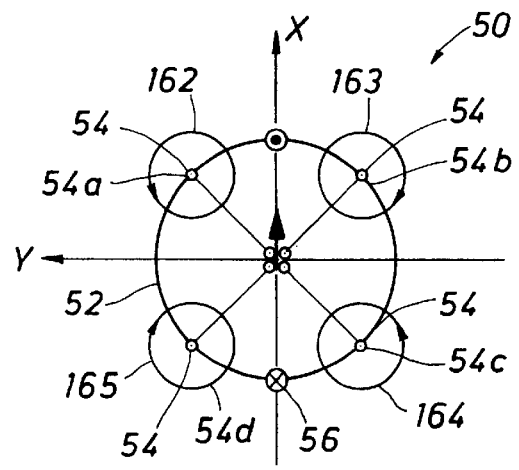
FIG. 3
FIG. 13

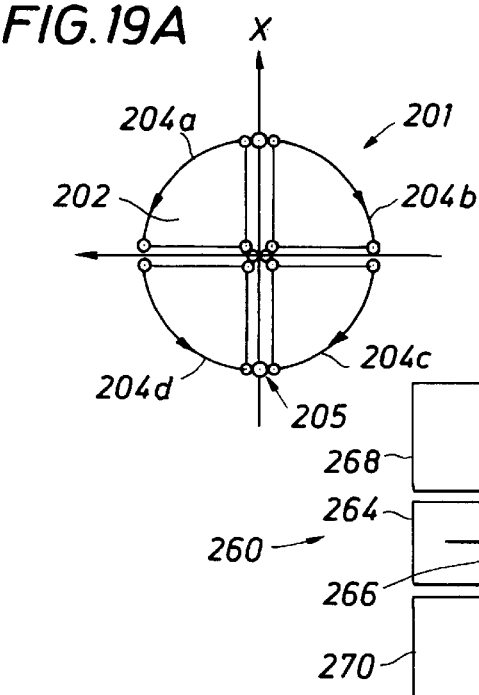
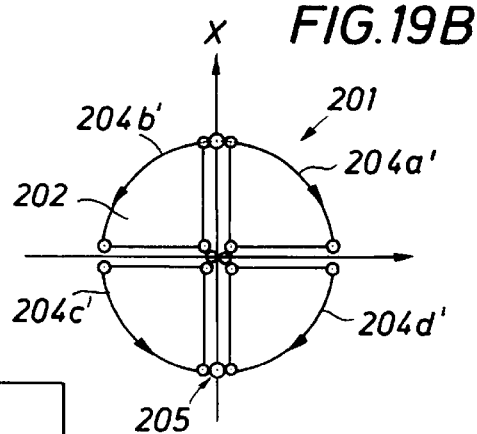
FIG. 19A  FIG. 19B
FIG. 25
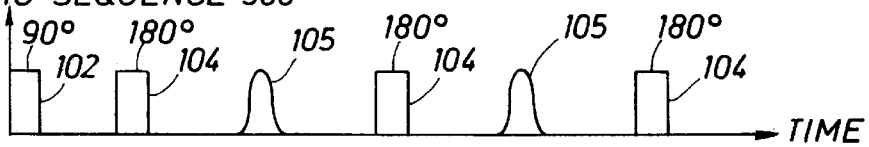
FIG. 26
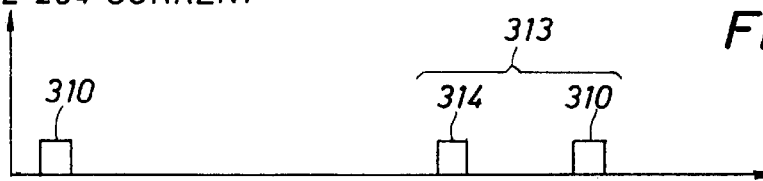
FIG. 27
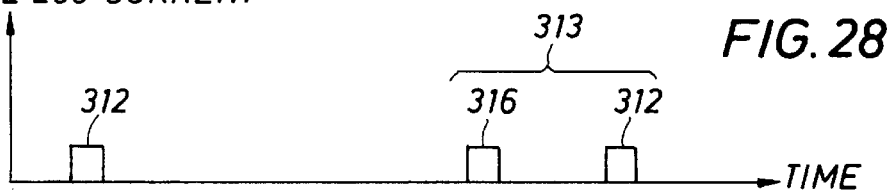
FIG. 28

SIGNALS ASSOCIATED
WITH CPMG
SEQUENCE 360

COIL 356a AND
COIL 356c CURRENT

COIL 356b AND
COIL 356d CURRENT

TWO-DIMENSIONAL MAGNETIC RESONANCE IMAGING IN A BOREHOLE

BACKGROUND

This invention generally relates to magnetic resonance imaging in a borehole.

Nuclear magnetic resonance (NMR) measurements typically are performed to investigate properties of a sample. For example, an NMR wireline or logging while drilling (LWD) downhole tool may be used to measure properties of subterranean formations. In this manner, a typical NMR tool may, for example, provide a lithology-independent measurement of the porosity of a particular formation by determining the total amount of hydrogen present in fluids of the formation. Equally important, the NMR tool may also provide measurements that indicate the dynamic properties and environment of the fluids, as these factors may be related to petrophysically important parameters. For example, the NMR measurements may provide permeability and viscosity information that is difficult or impossible to derive from other conventional logging arrangements. Thus, it is the capacity of the NMR tool to perform these measurements that makes it particularly attractive versus other types of downhole tools.

Typical NMR logging tools include a magnet that is used to polarize hydrogen nuclei (protons) in the formation and a transmitter coil, or antenna, that emits radio frequency (RF) pulses. A receiver antenna may measure the response (indicated by received spin echo signals) of the polarized hydrogen to the transmitted pulses. Quite often, the transmitter and receiver antennae are combined into a single transmitter/receiver antenna.

There are several experimental parameters that may be adjusted according to the objectives of the NMR measurement and expected properties of the formation fluids. However, the NMR techniques employed in current NMR tools typically involve some variant of a basic two step sequence that includes a polarization period followed by an acquisition sequence.

During the polarization period (often referred to as a "wait time") the protons in the formation polarize in the direction of a static magnetic field (called $B_0$) that is established by a permanent magnet (of the NMR tool). The growth of nuclear magnetization M(t) (i.e., the growth of the, polarization) is characterized by the "longitudinal relaxation time" (called T1) of the fluid and its maximum value (called $M_0$), as described by the following equation:

$$M(t) = M_0 \left(1 - e^{-\frac{t}{T_1}}\right) \quad \text{Equation 1}$$

The duration of the polarization period may be specified by the operator (conducting the measurement) and includes the time between the end of one acquisition sequence and the beginning of the next. For a moving tool, the effective polarization period also depends on tool dimensions and logging speed.

Referring to FIG. 1, as an example, a sample (in the volume under investigation) may initially have a longitudinal magnetization $M_Z$ 10 of approximately zero. The zero magnetization may be attributable to a preceding acquisition sequence, for example. However, the magnetization $M_Z$ 10 (under the influence of the $B_0$ field) increases to a magnetization level (called $M(t_w(1))$) after a polarization time $t_w(1)$ after zero magnetization. As shown, after a longer polarization time $t_w(2)$ from zero magnetization, the $M_Z$ magnetization 10 increases to an $M(t_w(2))$ level.

An acquisition sequence begins after the polarization period. For example, an acquisition W sequence may begin at time $t_w(1)$, a time at which the magnetization $M_Z$ 10 is at the $M(t_w(1))$ level. At this time, RF pulses are transmitted from a transmitter antenna of the tool. The pulses, in turn, produce spin echo signals 16, and the initial amplitudes of the spin echo signals 16 indicate a point on the magnetization $M_Z$ 10 curve, such as the $M(t_w(1))$ level, for example. Therefore, by conducting several measurements that have different polarization times, points on the magnetization $M_Z$ 10 curve may be derived, and thus, the T1 time for the particular formation may be determined. A receiver antenna (that may be formed from the same coil as the transmitter antenna) receives the spin echo signals 16 and stores digital signals that indicate the spin echo signals 16.

As an example, for the acquisition sequence, a typical logging tool may emit a pulse sequence based on the CPMG (Carr-Purcell-Meiboom-Gill) pulse sequence. The application of the CPMG pulse train includes first emitting an RF burst, called an RF pulse, that has the appropriate duration to rotate the magnetization, initially polarized along the $B_0$ field, by 90° into a plane perpendicular to the $B_0$ field. The RF pulse that rotates the magnetization by 90° is said to introduce a flip angle of 90°. Next, a train of equally spaced 180° RF pulses is transmitted. Each 180° RF pulse has the appropriate duration to rotate the magnet moment by 180° to refocus the spins to generate each spin echo signal 16. Each RF pulse that rotates the magnetization by 180° is said to introduce a flip angle of 180°. Individual hydrogen nuclei experience slightly different magnetic environments during the pulse sequence, a condition that results in an irreversible loss of magnetization and a consequent decrease in successive echo amplitudes. The rate of loss of magnetization is characterized by a "transverse relaxation time" (called T2) and is depicted by the decaying envelope 12 of FIG. 1.

In general, the above NMR measurement of the T1 time may be referred to as a saturation recovery, or T1-based, measurement due to the fact that the nuclear spins are saturated (i.e., the magnetization is decreased to approximately zero) at the beginning of the wait time. Thus, from the NMR measurement, a value of the magnetization $M_z$ 10 curve may be determined from the initial signal amplitude. In general, an NMR measurement of the signal decay may be labeled a T2-based measurement. It is noted that every T2 measurement is T1 weighted due to the fact that prepolarization occurs during the wait time before the acquisition sequence. The T2 time may be estimated from the observed decay of the envelope 12.

Referring to FIG. 2, for a particular NMR measurement, an NMR tool 30 establishes a resonance volume from which measurements of the sample are taken, such as a thin cylindrical resonance volume 32, for example. Unfortunately, the established resonance volume may be too large to yield the desired resolution. Therefore, high resolution images of the formation that surrounds the borehole may not be available. The resolution of the imaging along a longitudinal axis 34 of the borehole may be improved by decreasing the length of the RF coil. However, even with this technique, the axial resolution may be limited to approximately six to twenty-four inches. Furthermore, this technique does not provide a way to increase the resolution of the imaging in a tangential direction around the borehole.

Thus, there is a continuing need for an arrangement and/or technique to address one or more of the problems that are stated above.

SUMMARY

In an embodiment of the invention, a method that is usable with a downhole NMR measurement apparatus includes transmitting RF pulses pursuant to an NMR pulse sequence into a downhole formation that surrounds the NMR measurement apparatus. In response to the RF pulses, spin echo signals are received from a region of the formation. A pulsed gradient field in the downhole formation is generated during a time period in which the RF pulses are transmitted into the downhole formation; and the generation of the gradient field is controlled to phase encode the spin echo signals for purposes of high resolution imaging of the formation.

Advantages and other features of the invention will become apparent from the following description, drawing and claims.

BRIEF DESCRIPTION OF THE DRAWING

FIG. 3 is a schematic diagram of an NMR tool according to an embodiment of the a invention.

FIG. 13 is a cross-sectional view of the NMR tool taken along lines 13—13 of FIG. 3.

FIG. 19A is a top view of an NMR sensor according to an embodiment of the invention.

FIG. 19B is a bottom view of the NMR sensor of FIG. 19A according to an embodiment of the invention.

FIG. 25 is a front view of an NMR sensor according to an embodiment of the invention.

FIGS. 26, 27 and 28 are waveforms illustrating a pulsed gradient field technique for use with the NMR sensor of FIG. 25 according to an embodiment of the invention.

DETAILED DESCRIPTION

Figure 1:
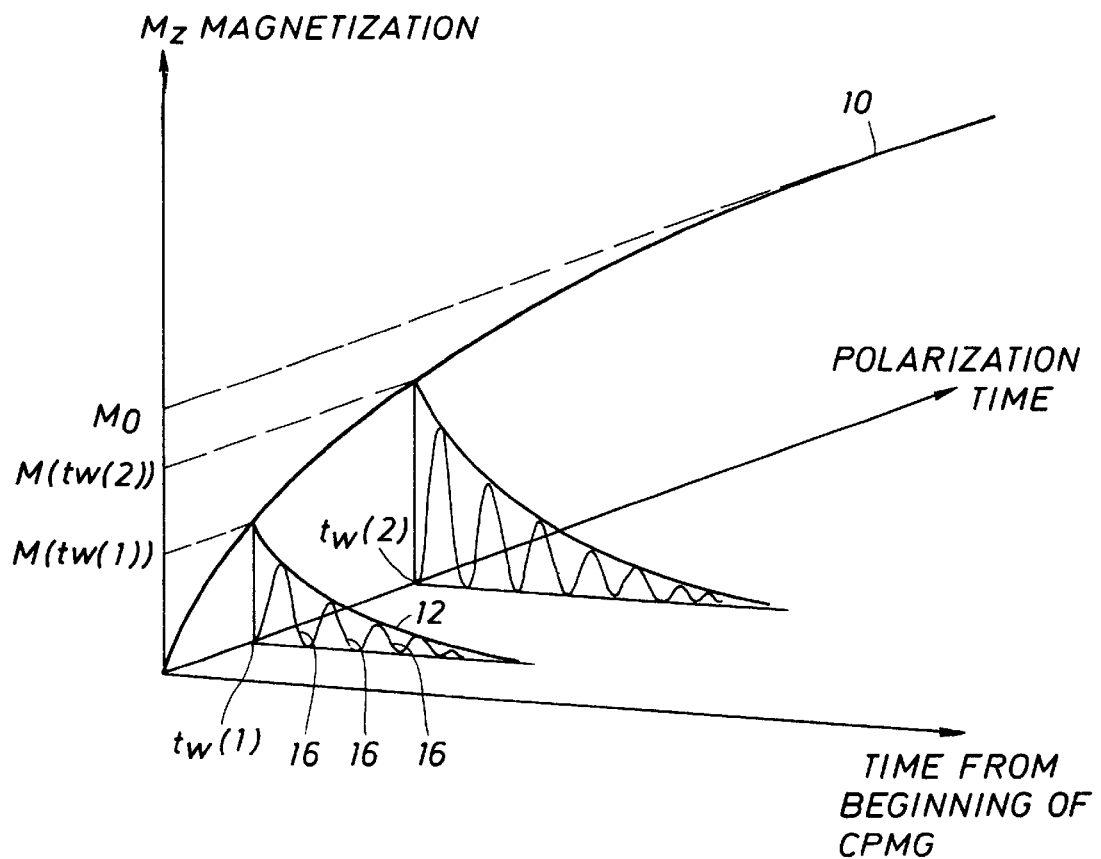
FIG. 1 is a graph of longitudinal magnetization illustrating T1 and T2 measurements of the prior art.
Figure 2:
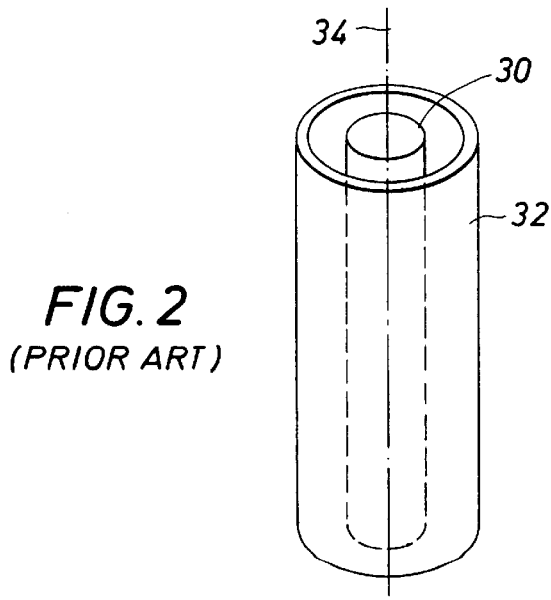
FIG. 2 is a schematic diagram illustrating a resonance volume that is established by an NMR tool of the prior art.

Referring to FIG. 3, an embodiment 50 of a downhole nuclear magnetic resonance (NMR) tool in accordance with the invention includes four gradient coils 54 (coils 54a, 54b, 54c and 54d, as examples) that the NMR tool 50 uses to produce pulsed gradient fields for purposes of producing a phase encoded gradient field. Due to this phase encoding, the NMR tool 50 may perform NMR measurements that yield information that can be used to produce higher resolution images than may be produced by using conventional downhole tools. As described below, the imaging techniques and arrangements described herein may be used for high resolution tangential imaging in a direction around the borehole and may be used for high resolution axial imaging along the longitudinal axis of the borehole.

For purposes of describing the operation of the NMR tool 50 and the other NMR tools and sensors described herein, a right-handed coordinate system is defined in which the z axis is defined (as shown in FIG. 3) along the longitudinal axis of the NMR tool 50 and borehole; an x axis is perpendicular to the z axis and is defined as the radial direction from the z axis toward the borehole; and a y axis is perpendicular to the z axis, perpendicular to the x axis, and is defined as extending in a tangential direction.

The NMR tool 50 may include an NMR sensor 51 that includes a permanent circularly cylindrical magnet 52 to establish a static magnetic field (called B.) along the x axis, although other orientations are possible in other embodiments of the invention, as described below. With the above-described polarization of the permanent magnet 52 along the x axis, an RF transmitting receiving coil 56 of the NMR sensor 51 has a magnetic moment along the y axis to produce RF pulses pursuant to an NMR pulse sequence so that spin echo signals are induced in the RF coil 56, as described below.

When performing the NMR pulse sequence, the NMR tool 50 controls currents through the gradient coils 54 to produce a pulsed tangential gradient field (as described below). This pulsed gradient field, in turn, varies the phases of the nuclear spins, as the different spins momentarily experience different magnetic field levels that, in turn, cause the spins to have tail different phases. Because the NMR tool 50 causes the gradient field to vary tangentially around the resonance volume, the locations of the parts of the formations that produce the spin echo signals are encoded into the spin echo signals. Although the NMR tool 50 uses the gradient coils 54 for purposes of obtaining high resolution tangential imaging, other NMR tools are described below that use pulsed gradient fields for purposes of obtaining high resolution axial imaging. Furthermore, the techniques and arrangements that are described herein may be used with an NMR tool for purposes of obtaining both high resolution axial and tangential imaging.

Besides the NMR sensor 51, the NMR tool 50 may include circuitry to generate RF pulses, receive spin echo signals and process the received spin echo signals. For example, in some embodiments of the invention, the NMR tool 50 may include a power supply 60 that furnishes the voltages that are used to generate the RF pulses. In this manner, an oscillator/amplifier 62 is coupled to the RF coil 52 and uses these voltages to generate the appropriate RF pulses. A controller 64 is coupled to the power supply 60, the oscillator/amplifier 62, the gradient coils 54 and the RF coil 52 to control the timing and other aspects of the RF pulses, the processing of the spin echo signals and the generation of the pulsed gradient field, as described below.

Figure 4:
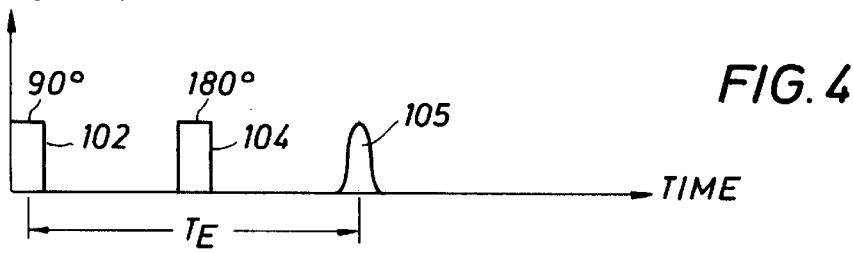
FIGS. 4, 5, 6, 7, 8, 9, 10, 11 and 12 are waveforms depicting pulsed gradient field techniques according to different embodiments of the invention.
Figure 5:

The following briefly explains techniques that may be used for purposes of establishing a pulsed gradient field in one-dimensional (1-D) image using the NMR tool 50 or other NMR tools that are described herein. As described below, these techniques may be expanded to generate a pulse tangential gradient field for purposes of tangential imaging. As an example, a particular technique to generate a 1-D pulsed gradient field along the y-axis (for example) may include using an NMR pulse sequence to induce spin echo signals from the formation, such as a Carr-Purcell-Meiboom-Gill (CPMG) sequence 100 (a portion of which is depicted in FIG. 4), and during the NMR pulse sequence, generating 1-D pulsed y gradient fields.

More particularly, in this technique, the NMR tool first applies a 90° tipping pulse 102 (pursuant to the CPMG sequence 100) to rotate the magnetization vector in the region of interest along the y axis in the rotating frame. The magnetization then starts to dephase, an event that is caused by inhomogeneity in the static field and the phase-encoding gradient that is applied after the 90° tipping pulse via a y gradient pulse 106. In this manner, the gradient pulse 106 momentarily establishes a gradient field along the y axis that causes spatially dependent phase differences between the spins, differences that encode the positions of the spins. At one half of the echo period (represented by "$T_E$"), the NMR tool applies a 180° refocusing pulse 104 (pursuant to the CPMG sequence 100) to reverse the precession of the magnetization. At the end of the $T_E$ echo period, the magnetization refocuses to induce a spin echo signal 105 in the RF receiving antenna of the NMR tool. The spin echo signal is encoded with the phase differences that were introduced by the pulsed y gradient field. Assuming that the applied gradient along the y axis is linear, the spin echo signal 105 may be described by the following equation:

$$M(t) = \int d\vec{r} M_0(\vec{r}) \exp \left\{ -i \left[ \int_0^{T_E/2} \omega_0(\vec{r}) dt' + \int_0^{T_y} \gamma G_y y dt' - \int_{T_E/2}^{t} \omega_0(\vec{r}) dt' \right] \right\},$$

Equation 2 where the minus signal is due to the 180° phase, "$G_y$" represents the field gradient along the y axis; "$\vec{r}$" represents a position vector; "$\omega_0$" represents the Larmor frequency; and "$T_y$" represents the duration of the gradient pulse 106.

As seen from Equation 2, the static field inhomogeneity is completely removed when $t=T_E$. The echo intensity depends on the strength of the gradient field intensity and the $T_y$ duration of the gradient pulse 106.

$$k_y = \int_0^{T_y} \gamma G_y dt,$$

Equation 3

Using $k_y$, the total echo intensity represented in k space becomes:

$$M(k_y) = \int dy m(y) e^{-iyk_y},$$

Equation 4 where $$m(y) = \int dx dz M_0(xyz) \int_{-T_a/2}^{T_a/2} dt' \exp -i[\omega(xyz)t'],$$

Equation 5 and "$T_a$" represents the duration of the acquisition window. $M(k_y)$ and $m(y)$ form a Fourier pair that images the $m(y)$ function in the y direction on the $M(k_y)$ function in the k space.

Using the basic NMR spin echo measurement sequence, the y gradient field is varied N times with equal increments, i.e., the pulsed gradient field is increased by $\Delta G$ that is described by the following equation:

$$\Delta G = \frac{G_{MAX} - G_{MIN}}{N - 1}$$

Equation 6 where "$G_{MIN}$" may be set equal to the negative of "$G_{MAX}$". The imaging of $m(y)$ may then be reconstructed by performing a Fourier transformation on a set of $\{M_i(ky,I)\}$ data, as described by the following equation:

$$m(y) = \frac{1}{2\pi} \int dk_y M(k_y) e^{iyk_y}$$

Equation 7

Because a CPMG sequence is used to generate a train of spin echo signals, there are numerous ways of phase encoding. The gradient field may be added between the 90° and 180° refocusing pulses or between adjacent 180° pulses, for example. Since the 180° pulse reverses the phases of the spins, the polarity of the gradient field may be reversed after each 180° refocusing pulse to accumulate the encoded phase. However, considering the imperfection of an RF pulse and the inhomogeneity of a static magnetic field, in some embodiments of the invention, the phase-encoding gradient is compensated before the next applied 180° refocusing pulse in order to take advantage of the compensation of the field inhomogeneity by the CPMG sequence. This compensation for a gradient placed after a 180° pulse may be implemented by applying the same gradient with an opposite sign before the next 180° refocusing pulse, as described below. In addition, the strength of the phase-encoded gradient is increased to increase the corresponding ky value.

Figure 6:
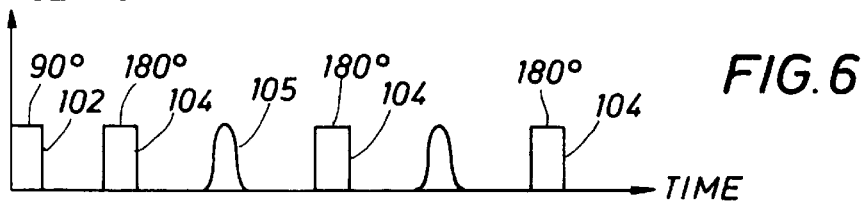
Figure 7:
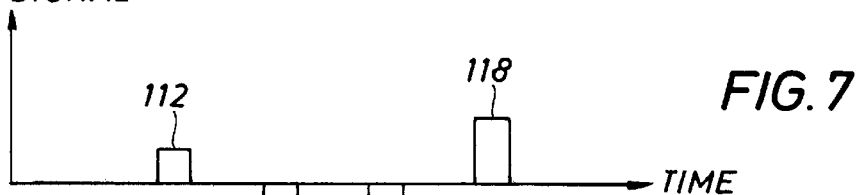

For example, FIG. 6 depicts a portion of a CPMG sequence 110 in which an 180° refocusing pulse 104 follows a 90° tipping pulse 102. The NMR tool applies a gradient pulse 112 (along the y axis ), as depicted in FIG. 7, after the 180° refocusing pulse 104. A spin echo signal 105 is then induced in the tool's RF receiving coil. Before the next 180° refocusing pulse 104, the NMR tool applies another y gradient pulse 114 along the negative y axis to remove the phase differences that were established by the gradient pulse 112. After the subsequent 180° refocusing pulse 104, the NMR tool applies a gradient pulse 116 with different amplitudes to establish a gradient along the negative y axis, which is compensated by the gradient pulse 118. It is noted that the gradient that is established by the gradient pulse 116 is larger than the magnitude of the gradient that is established by the gradient pulse 112. In this manner, the NMR tool controls the generation of the gradient pulses to increase magnitude of the applied pulsed gradient field for each measured spin echo signal.

Because the gradient field increases from one measured spin echo signal to the next, for a high $k_y$ value, the total power that is required to generate the gradient field pulses may become quite high. Due to the fact that the power storage capacity of the NMR tool is limited, an alternative technique that is depicted by a portion of a CPMG measurement sequence 120 in FIGS. 8 and 9 may be used in some embodiments of the invention.

In this manner, in some embodiments of the invention, the NMR tool may use another technique to increase the $k_y$ value with the echo number, a technique in which two pulsed gradient fields are applied in every other echo period: one gradient pulse 121 is generated just after a particular 180° refocusing pulse 104; and after the induced spin echo signal 105 and before the next 180° refocusing pulse, another gradient pulse 122 is generated. The next echo period (in which another spin echo signal 105 is generated) is skipped before the pulses 121 and 122 are generated in the subsequent echo period. This technique takes advantage of the error compensation of the CPMG sequence in that the CPMG sequence compensates the error caused by pulse imperfections and field inhomogeneity in every two echo periods. It is noted that the $k_y$ values increase using this technique without increasing the magnitude of the gradient pulses 121 and 122, thereby requiring less energy than the above-described techniques.

Other modifications to the above-described techniques are possible. For example, for purposes of maximizing the dynamic range of $k_y$, the sequence that is depicted in FIGS. 6 and 7 may be modified so that the magnitude of the first gradient pulse is $+G_{MAX}$, and the magnitude of the compensating gradient is $-G_{MAX}$. The magnitude of the next gradient is $(-G_{MAX}+\Delta G)$, followed by $(+G_{MAX}-\Delta G)$. The trend continues until the last pair are $-G_{MAX}$ and $+G_{MAX}$. This causes $k_y$ to vary from $-k_{yMAX}$ to $+k_{yMAX}$.

The use of an NMR tool with a shorter antenna and the use of a slower logging speed along the z axis provides a way to conventionally obtain better axial resolution than the azimuthal, or tangential, resolution. However, to improve the resolution along the z axis, the above-described techniques may be used to establish a pulsed z gradient field. Furthermore, both tangential and axial techniques may be combined for purposes of two-dimensional (2-D) imaging. For the z gradient, $k_z$ defined as follows:

$$k_z = \int_0^{T_y} \gamma G_z dt. \qquad \text{Equation 8}$$

With this definition of $k_z$, the echo intensity represented in k-space becomes:

$$M(k_y, k_z) = \int dy dz m(y, z) \exp{-i(yk_y + zk_z)}. \qquad \text{Equation 9}$$

The 2-D imaging of the borehole formation may be reconstructed by the 2-D inverse Fourier transformation given by the following equation:

$$m(y, z) = \frac{1}{(2\pi)^2} \int dk_y dk_z M(k_y, k_z) \exp(i(yk_y + zk_z)) \qquad \text{Equation 10}$$

Figure 9:
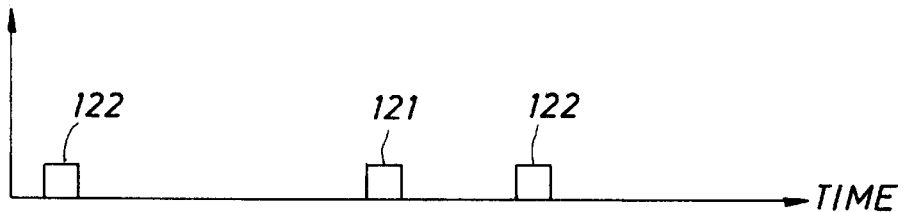
Figure 10:
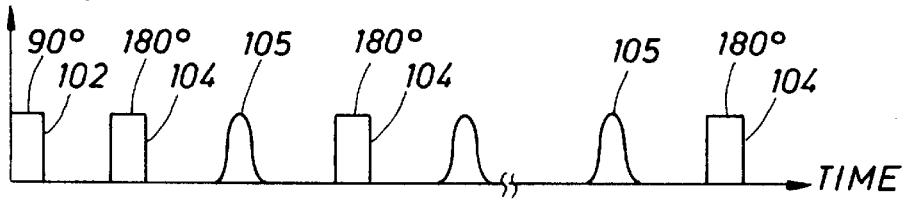
Figure 11:
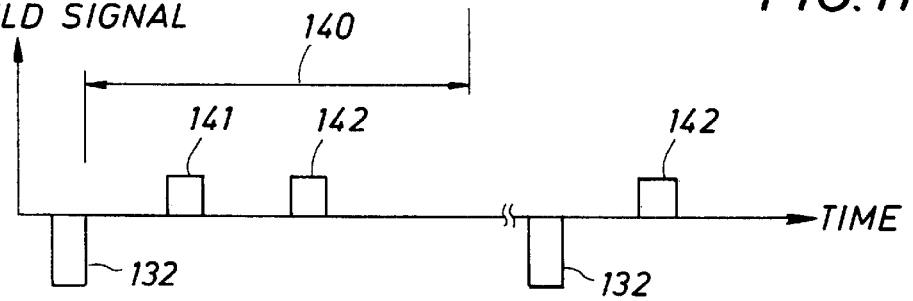
Figure 12:
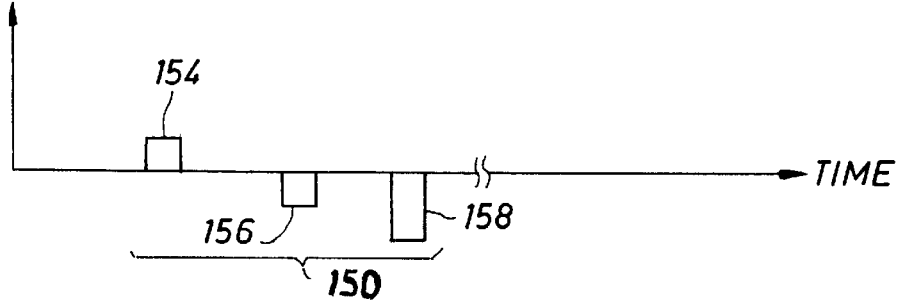
Figure 14:
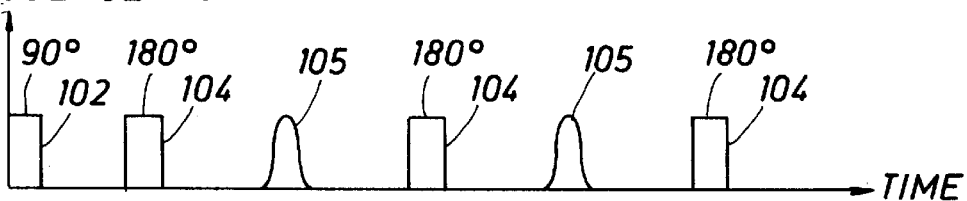
FIGS. 14, 15, 16, 17 and 18 are waveforms depicting a pulsed gradient field technique for use with the NMR tool of FIGS. 3 and 13 according to an embodiment of the invention.
Figure 15:
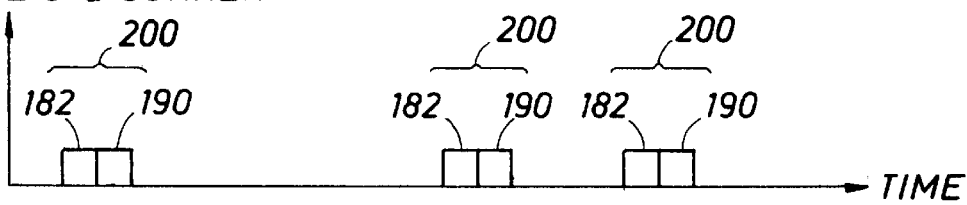
Figure 16:
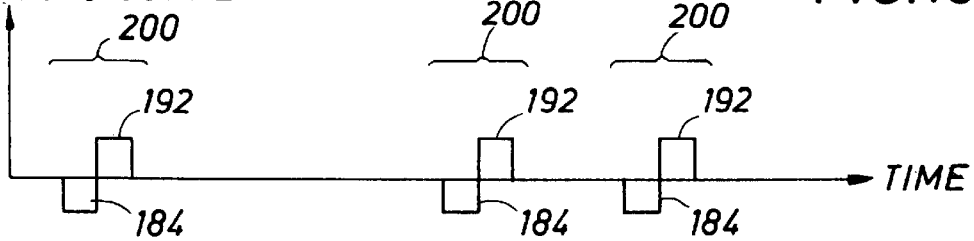
Figure 17:
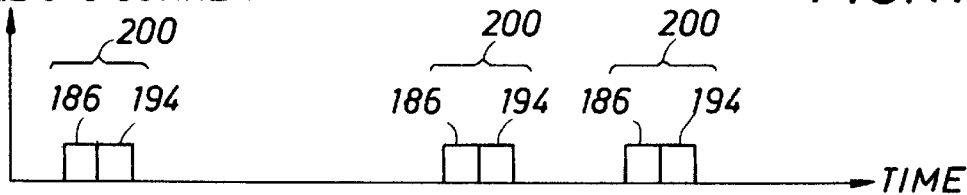
Figure 18:
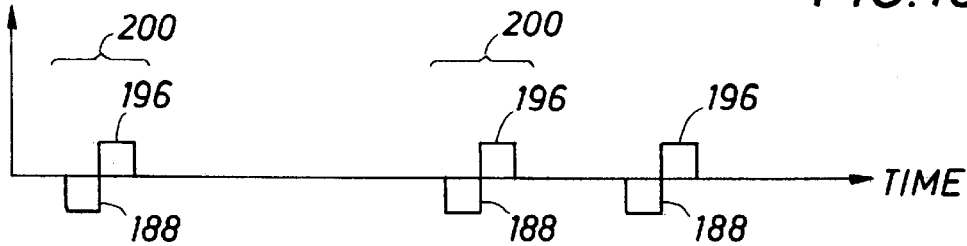
Figure 20:
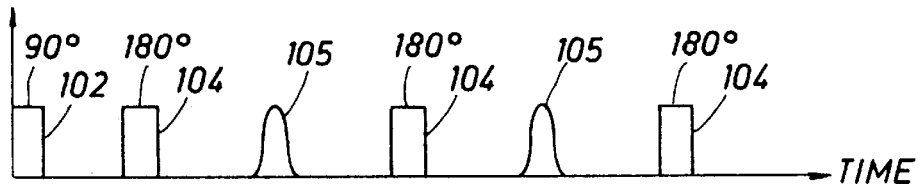
FIGS. 20, 21, 22, 23 and 24 are waveforms depicting a pulsed gradient field technique for use with the NMR sensor of FIGS. 19A and 19B according to an embodiment of the invention.
Figure 21:
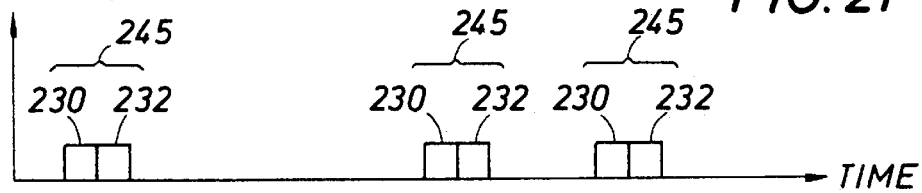
Figure 22:
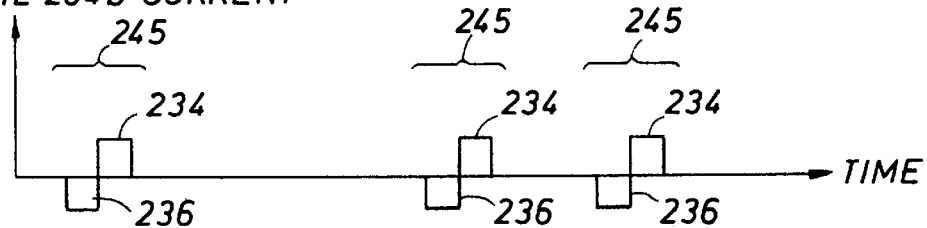
Figure 23:
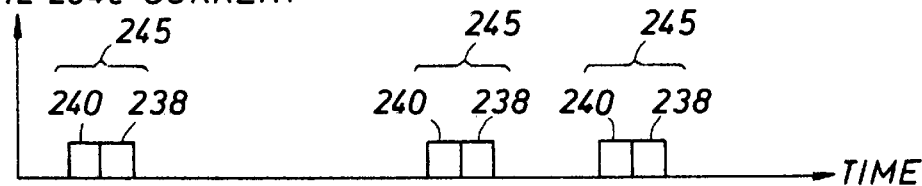
Figure 24:
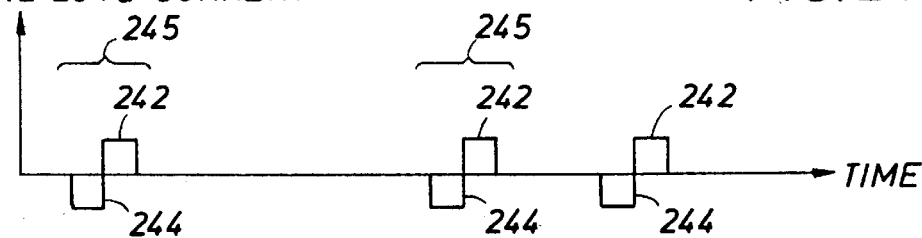

FIGS. 10, 11 and 12 represent a portion of a CPMG sequence 130 that may be used to image a borehole in two dimensions. In this manner, for tangential imaging, FIG. 11 depicts a sequence that starts with a gradient that has a magnitude of $-G_{MAX}$ causing $k_y$ to equal $-k_{yMAx}$. Then a sequence 140 is implemented that is similar to the sequence depicted in FIG. 9 in which pulsed gradients along the y axis are established by gradient pulses 141 and 142 that are applied in every other echo sequence. This increases $k_y$ to $-(k_{yMAx}+1)$. The sequence 140 of the gradient pulses 142 are repeated until $k_y$ equals $+k_{yMAx}$. For each sequence 140, a pulsed z gradient sequence 150 is generated, similar to the gradient pulse sequence that is depicted in FIG. 7, for example. In this manner for each N number of sequences 140 that are used to scan all of the tangential parts of the resonance volume, one of the gradient pulse sequences 150 is applied. Because the sequence 140 builds up the $k_y$ value to $k_{MAX}$, each sequence 140 is proceeded by a gradient pulse 132 that has a magnitude of $-G_{MAX}$ to destroy the phase differences before the beginning of the next sequence 140.

As depicted in FIG. 12, the z gradient pulses are applied between every two 180° refocusing pulses. The absolute magnitudes of the z gradient pulses are not changed until the completion of the N number of sequences 140. Thus, as an example, for a particular N number of sequences 140, the z-gradient pulses 154 and 156 are applied. The pulses 154 and 156 have the same absolute magnitude but opposite polarities. For the next N number of sequences, z-gradient pulses 158 (one pulse shown in FIG. 12) are applied. The pulses 158 have the same magnitudes (larger than the magnitudes of the pulses 154 and 156) but opposite polarities. The above-described relationship between the y and z gradient continues until the scan of the resonance volume is complete. Other variations are possible.

In the following description, specific NMR sensor designs are described according to different embodiments of the invention. In this manner, FIG. 13 depicts a cross-section of the NMR sensor 51 (of the NMR tool 50) that is illustrated in a perspective view in FIG. 3. As shown, the RF receiving/transmitting coil 56 has a magnetic moment that is aligned with the y axis. The magnet 52 is essentially diametrically polarized as a dipole to generate a static magnetic field (not shown in the figures) that exits the magnet 52 in a positive direction along the x axis and above the y axis and returns to the magnet 52 in a positive direction along the x axis and below the y axis. The static magnetic field $B_0$ that is generated by the magnet 52 may be described by the following equation:

$$\vec{B}_0 = \frac{B_r a^2}{2r^2}(\hat{x}\cos 2\theta + \hat{y}\sin 2\theta) \qquad \text{Equation 11}$$

where "$B_r$" represents the strength of the magnetic dipole, "a" represents the radius of the magnet 52, "r" represent the radial distance; "θ" represents the polar angle about the x axis; and "x" and "y" are unit vectors along the x and y axes, respectively. As can be seen from Equation 11, the magnitude of the dipolar magnetic field is independent of the polar angle.

The gradient coils 54 are equally spaced around the longitudinal axis of the magnet 52. In this manner, the gradient coil 54a approximately lies in a plane that contains the z axis and is located midway between the x axis and the y axis. The gradient coil 54a includes a portion that is parallel to the z axis and is located near the outer surface of the magnet 52 in the quadrant between the positive x and y axes. This portion of the gradient coil 54a produces field lines that, when positive current flows through the coil 54a, circumscribe the portion in a counterclockwise direction that is depicted by an exemplary field line 162 in FIG. 13. The gradient coil 54a radially traverses across the magnet 52 at the two ends of the coil 54a between the exterior surface of the magnet 52 and the center of the magnet 52, and the remaining part of the gradient coil 54a is formed by a section that extends near the center of the magnet 52 along the z axis.

The gradient coil 54c also lies in the plane that contains the gradient coil 54a, but the gradient coil 54c is located on the opposite side of the z axis from the gradient coil 54a in a quadrant between the negative x and negative y axes. The gradient coil 54c includes a portion that is parallel to the z axis and is located near the outer surface of the magnet 52 in the quadrant between the negative x and negative y axes. This portion of the gradient coil 54c produces field lines that, when positive current flows through the coil 54c, circumscribe the portion in a counterclockwise direction that is depicted by an exemplary field line 164 in FIG. 13. The gradient coil 54c radially traverses across the magnet 52 at the two ends of the coil 54b between the exterior surface of the magnet 52 and the center of the magnet 52, and the remaining part of the gradient coil 54c is formed by a section that extends near the center of the magnet 52 along the z axis.

The gradient coil 54b approximately lies in a plane that contains z axis and is located midway between the positive x axis and the negative y axis. The gradient coil 54b includes a portion that is parallel to the z axis and is located near the outer surface of the magnet 52 in the quadrant between the positive x axis and the negative y axis. This portion of the gradient coil 54b produces field lines that, when positive current flows through the coil 54b (as depicted in FIG. 13), circumscribe the portion in a clockwise direction that is depicted by an exemplary field line 163 in FIG. 13. When the current flows in an opposite direction through the coil 54b, the field lines circumscribe the portion in a counterclockwise direction. The gradient coil 54b radially traverses across the magnet 52 at the two ends of the coil 54b between the exterior surface of the magnet 52 and the center of the magnet 52, and the remaining part of the gradient coil 54b is formed by a section that extends near the center of the magnet 52 along the z axis.

The gradient coil 54d approximately lies in a plane that contains z axis and is located midway between the positive y axis and the negative x axis. The gradient coil 54d includes a portion that is parallel to the z axis and is located near the outer surface of the magnet 52 in the quadrant between the positive y axis and the negative x axis. This portion of the gradient coil 54d produces field lines that, when positive current flows through the coil 54d (as depicted in FIG. 13), circumscribe the portion in a clockwise direction that is depicted by an exemplary field line 165 in FIG. 13. When the current flows in an opposite direction through the coil 54d, the field lines circumscribe the portion in a counterclockwise direction. The gradient coil 54d radially traverses across the magnet 52 at the two ends of the coil 54d between the exterior surface of the magnet 52 and the center of the magnet 52, and the remaining part of the gradient coil 54d is formed by a section that extends near the center of the magnet 52 along the z axis. The gradient coil 54d also lies in the plane that contains the gradient coil 54b, but the gradient coil 54d is located on the opposite side of the z axis from the gradient coil 54b in a quadrant between the negative x axis and the positive y axis.

The controller 64 (see FIG. 3) selectively activates the gradient coils 54a, 54b, 54c and 54d to pulse the x and y gradient fields for purposes of producing a pulsed tangential gradient field. In this manner, referring to FIGS. 14, 15, 16, 17 and 18, the controller 64 generates a sequence 200 in which the controller 64 concurrently pulses the gradient coils 54a (via a current pulse 182) and 54c (via a current pulse 186) with positive currents and pulses the gradient coils 54b (via a current pulse 184) and 54d (via a current pulse 188) with negative currents to establish a pulsed gradient field along the y axis; and subsequently, the controller 200 concurrently pulses all of the gradient coils 54a (via a current pulse 190), 54b (via a current pulse 192), 54c (via a current pulse 194) and 54d (via a current pulse 196) with positive currents to establish a gradient field along the x axis. Collectively, the pulsed x and y gradient fields establish a pulsed tangential gradient field. In this manner, the latter part of the sequence 200 is necessary for purposes of distinguishing specific regions of the resonance volume 51, as the y gradient field is symmetrical about the y axis and the x gradient field is symmetrical about the x axis. Therefore, in combination, the two parts of the sequence 200 establish a tangential gradient.

Figure 8:
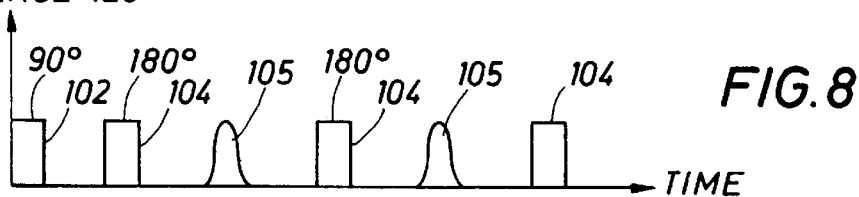

The controller 64 applies the sequence 200 in every other echo sequence of a CPMG sequence 170 for purposes of gradually increasing the k values that are associated with the tangential gradient field. Thus, this technique is analogous to the technique that is depicted in FIGS. 8 and 9 for the case of the y gradient.

FIGS. 19A and 19B depict top and bottom views, respectively, of an NMR sensor 201 of another NMR tool according to another embodiment of the invention.

The NMR sensor 201 includes a cylindrical permanent magnet 202 that is coaxial with the z axis (that points out of the page) and is polarized along the z axis. The NMR sensor 201 also includes RF receiving/transmitting coil 205. Referring to FIG. 19A, the sensor 201 includes a flat gradient coil 204a that located on a top surface of the magnet 202 and thus, lies in a plane that is orthogonal to the z axis. When the gradient coil 204a receives a positive current, the current in the gradient coil 204a flows along the curved portion from the x axis toward the y axis. The gradient coil 204a' (see FIG. 19B) is located on the bottom surface of the magnet 202 and is aligned with the gradient coil 204a. In this manner, the gradient coil 204a' also circumscribes one quarter of a circle, and the curved portion of the gradient coil 204a' extends along the outer periphery of the bottom surface of the magnet 202 between the x and y axes. When the gradient coil 204a' receives a positive current, the current in the gradient coil 204a' flows along the curved portion from the x axis toward the y axis.

The NMR sensor 201 also includes a flat gradient coil 204b that located on the top surface of the magnet 202 and thus, lies in a plane that is orthogonal to the z axis. The gradient coil 204b circumscribes one quarter of a circle that circumscribes the top surface of the magnet 202. The curved portion of the gradient coil 204b extends along outer periphery of the top surface of the magnet 202 between the positive x and negative y axes. When the gradient coil 204b receives a positive current, the current in the gradient coil 204b flows along the curved portion from the positive x axis toward the negative y axis. The gradient coil 204b' (see FIG. 19B) is located on the bottom surface of the magnet 202 and is aligned with the gradient coil 204b. In this manner, the gradient coil 204b' also circumscribes one quarter of a circle, and the curved portion of the gradient coil 204b' extends along the outer periphery of the bottom surface of the magnet 252 between the positive x axis and the negative y axis. When the gradient coil 204b' receives a positive current, the current in the gradient coil 204b' flows along the curved portion from the positive x axis toward the negative y axis.

A flat gradient coil 204c of the sensor 201 is located on the top surface of the magnet 202 and thus, lies in a plane that is orthogonal to the z axis. The gradient coil 204c circumscribes one quarter of a circle that circumscribes the top of the magnet 202. The curved portion of the gradient coil 204c extends along outer periphery of the top surface of the magnet 202 between the negative x axis and the negative y axis. When the gradient coil 204c receives a positive current, the current in the gradient coil 204c flows along the curved portion from the negative y axis toward the negative x axis. The gradient coil 204c' (see FIG. 19B) is located on the bottom surface of the magnet 202 and is aligned with the gradient coil 204c. In this manner, the gradient coil 204c' also circumscribes one quarter of a circle, and the curved portion of the gradient coil 204c' extends along the outer periphery of the bottom surface of the magnet 202 between the negative x and negative y axes. When the gradient coil 204c' receives a positive current, the current in the gradient coil 204c' flows along the curved portion from the negative x axis toward the negative y axis.

The fourth set of gradient coils of the sensor 201 includes a gradient coil 204d and a gradient coil 204d'. The flat gradient coil 204d that located on the top surface of the magnet 202 and thus, lies in a plane that is orthogonal to the z axis. The gradient coil 204d circumscribes one quarter of a circle that circumscribes the top surface of the magnet 202. The curved portion of the gradient coil 204d extends along outer periphery of the top of the magnet 202 between the negative x axis and the positive y axis. When the gradient coil 204d receives a positive current, the current in the gradient coil 204d flows along the curved portion from the negative x axis toward the positive y axis. The gradient coil 204d' (see FIG. 19B) is located on the bottom surface of the magnet 202 and is aligned with the gradient coil 204d. In this manner, the gradient coil 204d' also circumscribes one quarter of a circle, and the curved portion of the gradient coil 204d' extends along the outer periphery of the bottom surface of the magnet 202 between the negative x axis and the positive y axis. When the gradient coil 204d' receives a positive current, the current in the gradient coil 204d' flows along the curved portion from the negative x axis toward the positive y axis Referring to FIGS. 20, 21, 22, 23 and 24, the NMR sensor 201 may be operated in the following manner. Similar to the NMR tool 50, gradients are established by the sensor 201 via two step sequences 245 that occur in alternating spin echo sequences. In this manner, in each sequence 245, the first step includes concurrently pulsing the gradient coils 204a, 204a', 204c and 204c' with positive current (via positive current pulses 230 and 240, respectively) and pulsing the gradient coils 204b, 204b', 204d and 204d' with negative current (via negative current pulses 236 and 244, respectively) to establish an x gradient field. Because of the symmetry of the x gradient field about the x axis, the second step is required in the sequence 245, a step that includes concurrently pulsing all of the gradient coils 204a, 204a', 204b, 204b', 204c, 204c', 204d and 204d' with positive current (via positive current pulses 232, 234, 238 and 242, respectively) to establish a y gradient field. Collectively, the x and y gradient fields form a pulsed tangential gradient field, the magnitude of which is increased over the course of a CMPG sequence 220, as described above.

FIG. 25 depicts an NMR sensor 260 according to another embodiment of the invention. The sensor 260 includes an upper circularly cylindrical permanent magnet 268 that has its longitudinal axis aligned with the z axis. The magnet 268 is polarized along the positive z axis.

The sensor 260 also includes a lower cylindrical magnet 270 that is located below the upper magnet 268. The magnet 270 has its longitudinal axis aligned with the z axis, and the magnet 270 is polarized along the negative z axis. An RF receiving/transmitting coil 265 of the sensor 260 is located between the upper 268 and lower 270 magnets and has a magnetic moment that is aligned with the z axis.

The NMR sensor 260 includes a rectangular gradient coil 264 that is located between the upper 268 and lower 270 magnets and has a magnetic moment along the x axis (coming out of the page in FIG. 25) for purposes of establishing a y gradient field. The sensor 260 also includes another rectangular gradient coil 266 that has a magnet moment along the y axis for purposes of establishing an x gradient field. In combination, the two gradient coils 264 and 266 may be used in combination to produce a tangential gradient field, as depicted in FIGS. 26, 27 and 28, during a CPMG sequence 300. In this manner, the gradient coils 264 and 266 are successively pulsed high via current pulses 314 and 316, respectively, and then pulsed high again via current pulse 310 and 312, respectively, during a sequence 313, to establish a particular tangential field. This sequence 313 occurs in every other echo sequence to gradually build up the magnitude of the pulsed tangential gradient field during the CPMG sequence.

Figure 29:
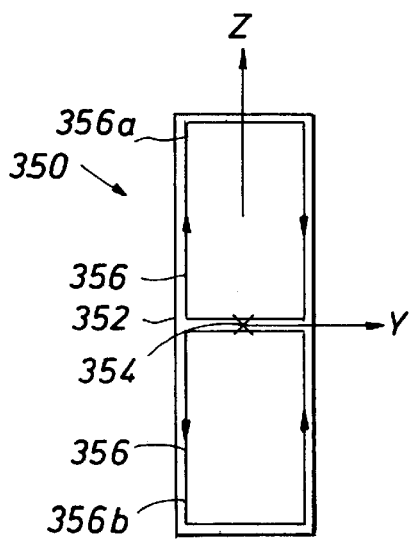
FIG. 29 is a front view of an NMR sensor according to an embodiment of the invention.
Figure 30:
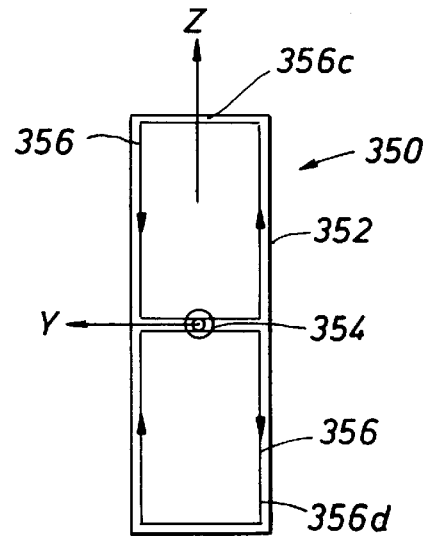
FIG. 30 is a rear view of the NMR sensor of FIG. 29 according to an embodiment of the invention.

The embodiments that are described above address tangential imaging. FIGS. 29 and 30 depict an NMR sensor 350 to enhance the vertical, or axial, resolution along the z axis. A small axial resolution may be useful for imaging thinbed formations, for example. The sensor 350 includes a permanent cylindrical magnet 352 that has its longitudinal axis aligned with the z axis and is diametrically polarized so that the magnetic moment of the magnet 352 is aligned with the x axis (that points out of the page). An RF coil 354 of the sensor 350 has a magnetic moment that is aligned with the z axis.

The sensor 350 includes four surface gradient coils 356a, 356b, 356c and 356d to establish a z gradient field. In this manner, the gradient coils 356a and 356c are located on the front and back sides, respectively, of the magnet 352 and are located above the RF coil 354. Each gradient coil 356a, 356c has a magnetic moment that is oriented along the negative x axis (the positive x axis is coming out of the page) when the coil 356a, 356c receives a positive current. The gradient coils 356b and 356d are located on the front and back sides, respectively, of the magnet 352 and are located below the RF coil 354. Each gradient coil 356b, 356cd has a magnetic moment that is oriented along the positive x axis (the positive x axis is coming out of the page) when the coil 356b, 356d receives a positive current.

Figure 31:
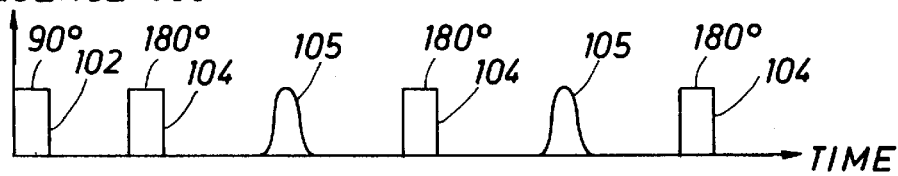
FIGS. 31, 32 and 33 are waveforms depicting a pulsed gradient field technique to use with the NMR sensor of FIGS. 29 and 30 according to an embodiment of the invention.
Figure 32:
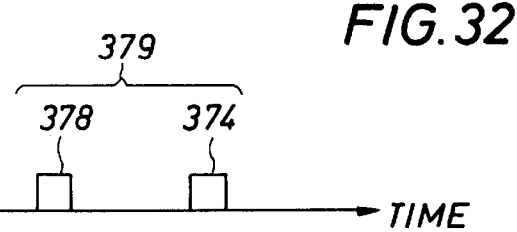
Figure 33:
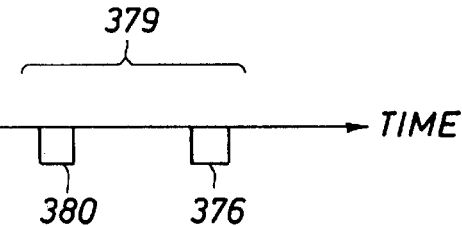

Referring to FIGS. 31, 32 and 33, due to the above-described arrangement, in a sequence 379, the gradient coils 356a and 356c may be pulsed, before the spin echo signal 105, with positive current pulses 378 at the same time that the gradient coils 356b and 356d are pulsed with a negative current pulses 380 to establish the z gradient field. This pulsing described above occurs after the spin echo signal 105 in the sequence 379. The sequence 379 occurs in every other echo sequence of a CPMG sequence 360 to gradually increase the magnitude of the pulsed z gradient for purposes of axial imaging.

Figure 34:
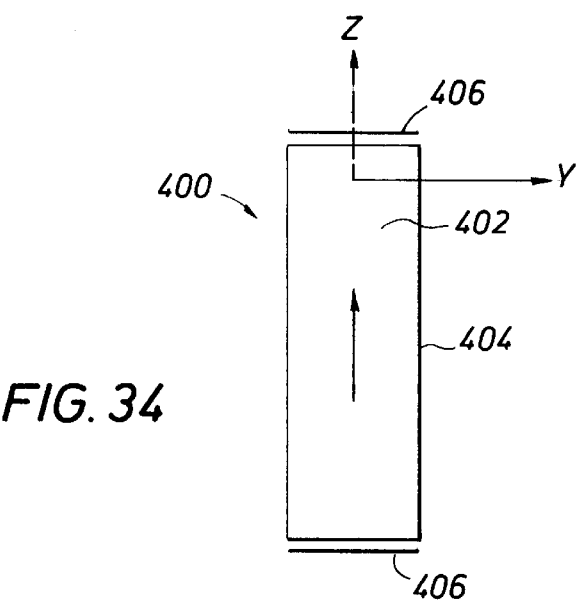
FIG. 34 is a front view of an NMR sensor according to an embodiment of the invention.

FIG. 34 depicts another NMR sensor 400 that may be used for purposes of high resolution axial borehole imaging according to another embodiment of the invention. The NMR sensor 400 includes a cylindrical permanent magnet 402 that is coaxial with the z axis and is polarized so that the magnetic moment of the magnet 402 is directed in a positive direction along the z axis. An RF receiving/transmitting coil 404 extends around the outer periphery of the magnet 402 to circumscribe the x axis (that points out of the page).

Figure 35:
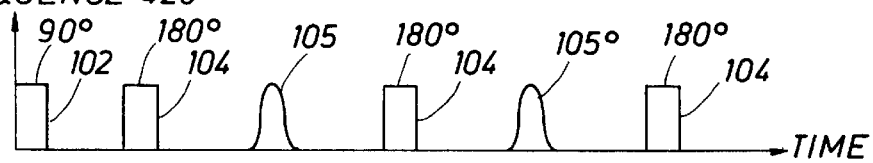
FIGS. 35, 36 and 37 are waveforms illustrating a pulsed gradient field technique for use with the NMR sensor of FIG. 34 according to an embodiment of the invention.
Figure 36:
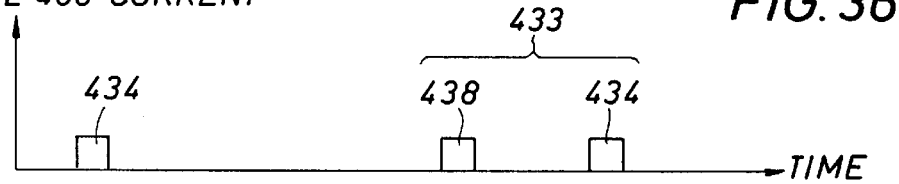
Figure 37:
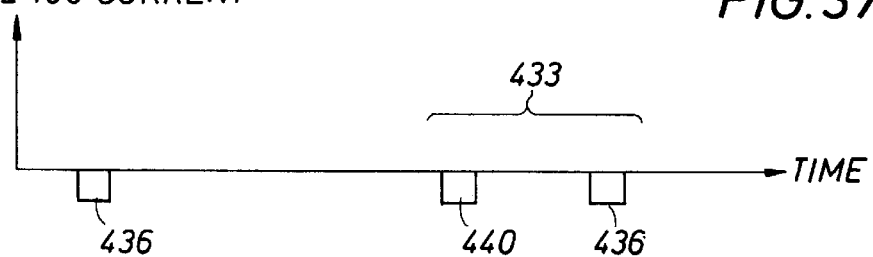

The NMR sensor 400 includes an upper gradient coil 406 that is located at the top surface of the magnet 402 to produce a magnet moment that is directed along the positive z axis when the upper gradient coil 406 receives a positive current and a lower gradient coil 408 that is located at the bottom surface of the magnet 402 to produce a magnetic moment that is directed along the positive z axis when the gradient coil 408 receives a positive current. Referring to FIGS. 35, 36 and 37, before a spin echo signal 105 occurs during a CPMG sequence 420, a sequence 433 includes pulsing the gradient coil 406 with a positive current pulse 438 at the same time that the gradient coil 408 is pulsed with a negative current pulse 440 to produce a z gradient field. The concurrent pulsing occurs again (via current pulses 434 and 436) after the spin echo signal 105 to complete the sequence 433. The sequence 433 may be generated in every other echo interval of the CPMG sequence 420, as described above.

Figure 38:
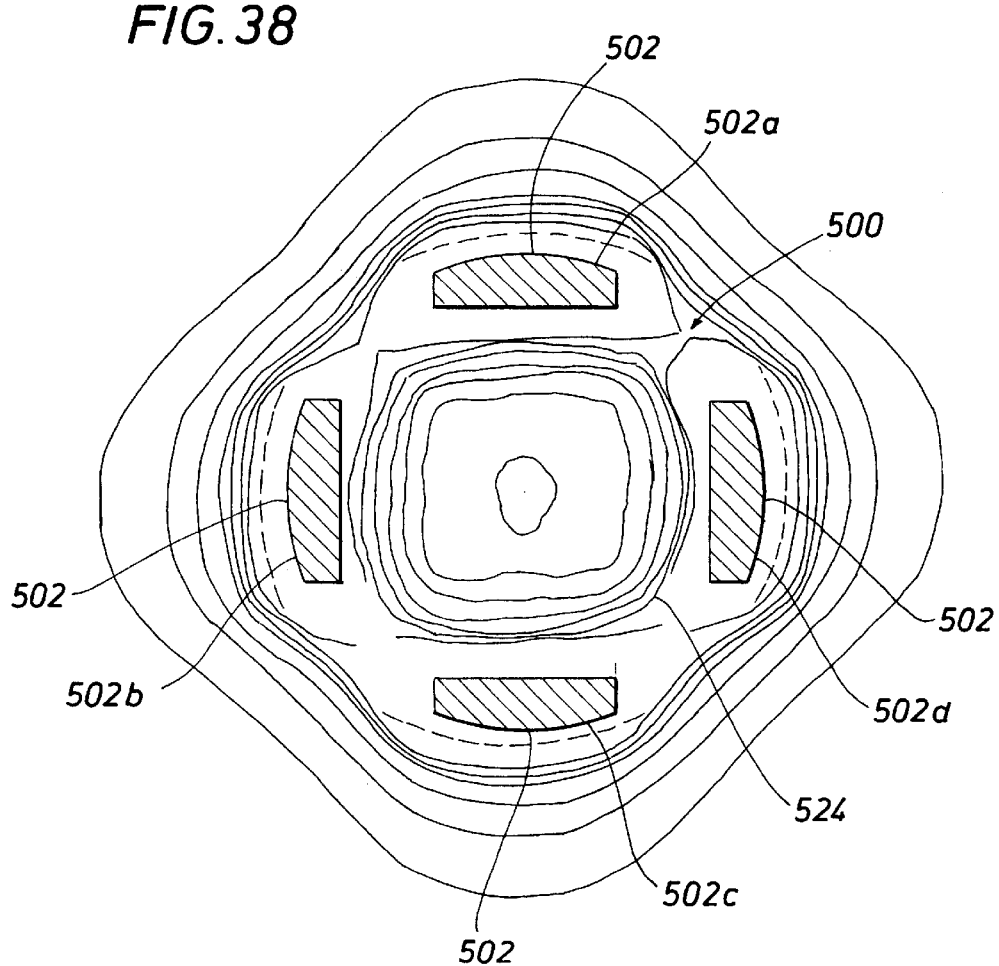
FIG. 38 is a cross-sectional view of an NMR sensor according to an embodiment of the invention.

Techniques other than the techniques that are described above may be used to improve imaging resolution. For example, FIG. 38 depicts a cross-section of an NMR sensor 500 according to another embodiment of the invention.

Figure 40:
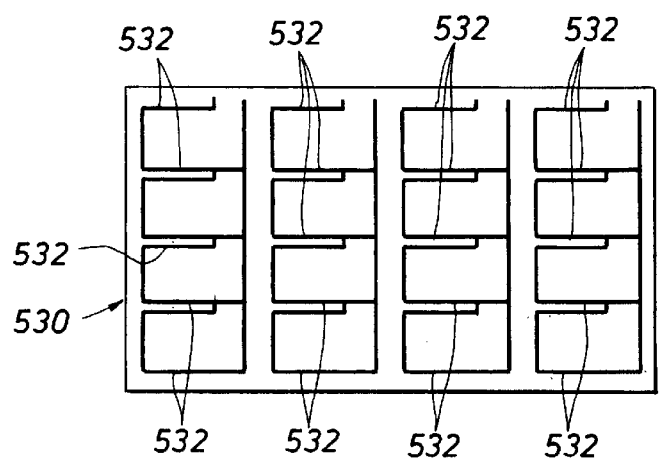
FIG. 40 is a schematic diagram of a receiver coil array of the NMR tool of FIG. 39 according to an embodiment of the invention.
Figure 39:
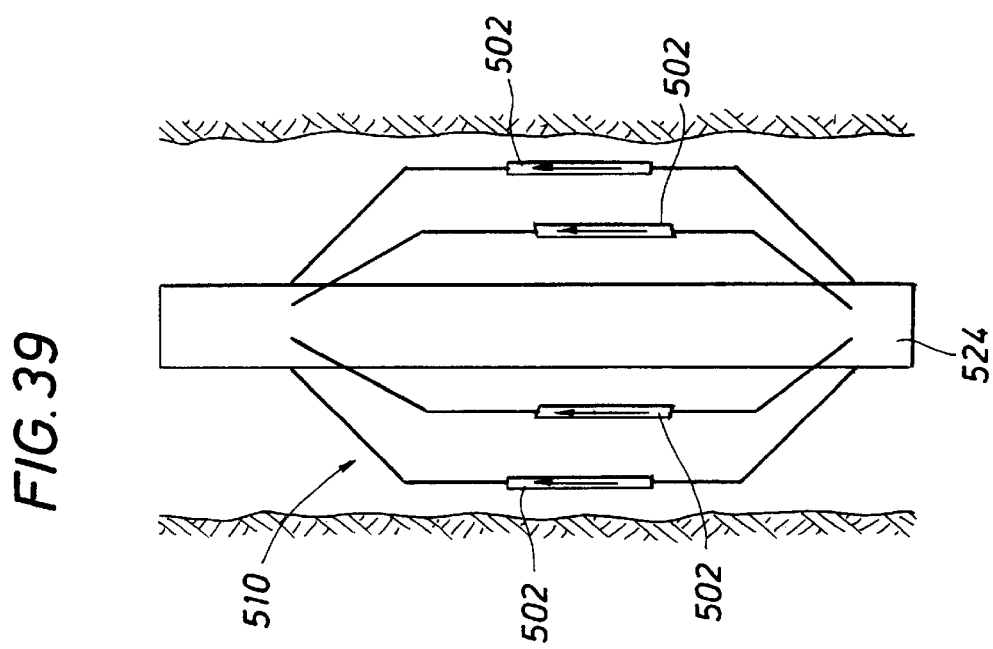
FIG. 39 is a perspective view of an NMR tool according to an embodiment of the invention.

The NMR sensor 500 includes sensor pads 502 (sensor pads 502a, 502b, 502c and 502d, as examples) that are spaced apart around the longitudinal axis of the sensor 500 for purposes of performing NMR measurements. Referring also to the NMR sensor 510 of FIG. 39, the pads 502 circumscribe a cylindrical permanent magnet 524 of the sensor 500, and each pad 520 includes an array 530 of surface coils 532 that is depicted in FIG. 40. In this manner, the surface coils 532 are small coils that are arranged in rows and columns (as an example) for purposes of selectively imaging different adjacent regions of the resonance volume. Each surface coil 532 may form a separate RF receive antenna for imaging an associated region of the borehole 503. Alternatively, groups of surface coils 532 of the array 530 may be used to image an associated region of the borehole. For example, each column of surface coils 532 may be used to image a different section of the borehole 503 to improve the tangential resolution of the imaging.

As examples, the permanent magnet 524 (see FIG. 39) may be either diametrically polarized or polarized along its longitudinal axis. Alternatively, two permanent magnets may replace the permanent magnet 524 in an arrangement similar to the configuration of the permanent magnets and RF coil that is depicted in FIG. 25. Other arrangements are possible.

Figure 41:
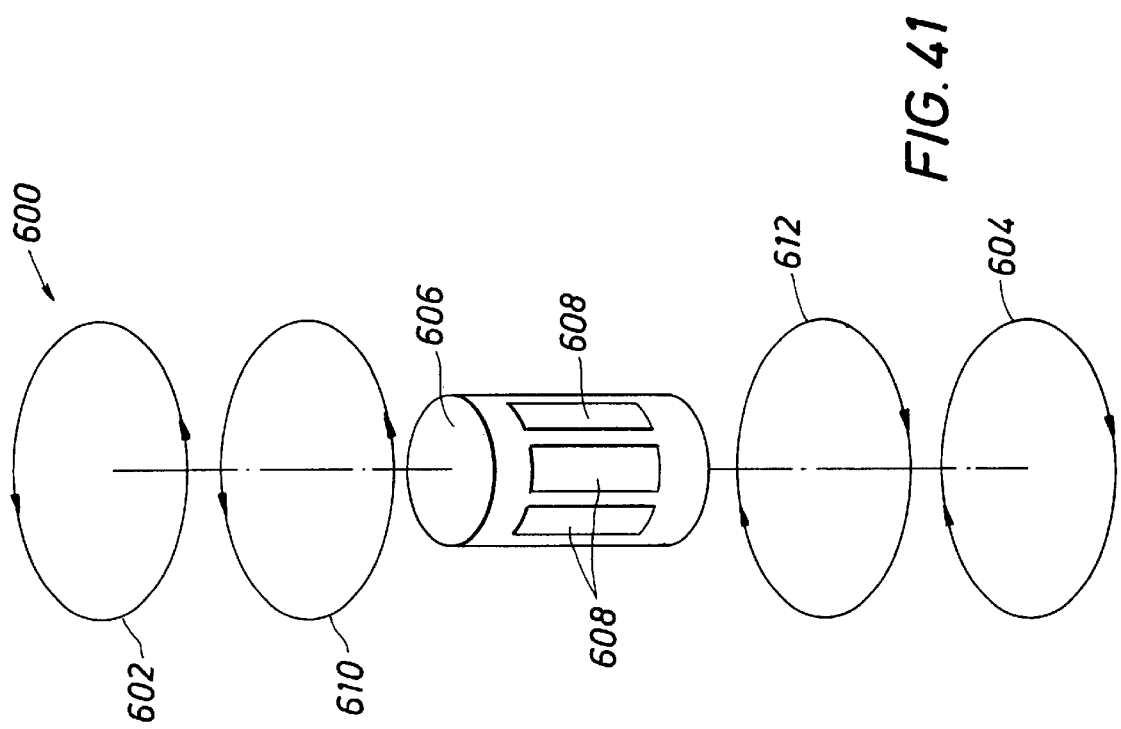
FIG. 41 is an exploded perspective view of an NMR tool according to another embodiment of the invention.

The techniques and arrangements that are described above may be combined to produce other NMR sensors. For example, referring to FIG. 41, an NMR sensor 600 may include a cylindrical permanent magnet 606 that is circumscribed by arrays 608 of RF receiver coils for purposes of high resolution tangential imaging. The NMR sensor 600 may also include an upper gradient coil 602 and a lower gradient coil 604 that are arranged in a manner to produce a z gradient field for high resolution axial imaging, similar to the axial imaging arrangement that is depicted in FIG. 34 and described in the corresponding text. The NMR sensor 600 may, in some embodiments of the invention, include RF transmitter coils 610 and 612, each of which has its magnet moment extending along the longitudinal axis of the permanent magnet 606. Alternatively, RF receiver coils of the arrays 608 may also be used for RF transmission purposes.

The various embodiments of the invention described herein, such as sensors 51, 201, 260, 350, 400, 500, and 600, can also be used with well logging apparatus forming part of a drilling tool string. Well logging apparatus forming part of a drilling tool string are generally adapted to make measurements of formation properties by moving the drilling tool string along the wellbore. Moving the drilling tool string generally takes place during the drilling of a wellbore by a drill bit but also includes "pipe trips" where the drilling tool string is partially or totally removed from the wellbore. Such well logging instruments are known in the art as logging-while-drilling (LWD) instruments. Such LWD instruments are described, for example, in U.S. Pat. No. 5,757,186 issued to Taicher et al., U.S. Pat. No. 5,280,243 issued to Miller, published PCT application WO 99/36801 filed by Prammer et al and assigned to Numar Corporation, and published European application 0 581 666 filed by Kleinberg et al and assigned to the assignee of the present invention.

What is claimed is:

1. A method usable with a downhole NMR measurement apparatus, comprising using a magnet to polarize spins in a downhole formation that surrounds the NMR measurement apparatus;

transmitting RF pulses pursuant to an NMR pulse sequence into the downhole formation;

in response to the RP pulses, receiving spin echo signals from a region of the formation;

generating a pulse gradient field in the downhole formation;

controlling the generation of the pulsed gradient field to phase encode the spin echo signals; and imaging at least one formation evaluation characteristic, independent of fluid flow within the formation, based on the phase encoded spin echo signals for at least a two-dimensional region of the downhole formation that circumscribes the NMR measurement apparatus.

2. The method of claim 1, wherein the generating the pulsed gradient field comprises:

progressively increasing a magnitude of the pulsed gradient field.

3. The method of claim 1, wherein the generating the pulsed gradient field comprises:

pulsing at least one gradient coil with a current.

4. The method of claim 1, wherein the NMR pulse sequence comprises successive refocusing pulses, each refocusing pulse producing a spin echo signal that precedes the next successive refocusing pulse in time; and generating the pulsed gradient field comprises:

for every other spin echo signal, pulsing at least one gradient coil with a current before said every other spin echo signal and after the last refocusing pulse and pulsing said at least one gradient coil with the current after said every other spin echo signal and before the next refocusing pulse.

5. The method of claim 1, wherein the pulsed gradient field is approximately tangential to the NMR measurement apparatus.

6. The method of claim 1, wherein the pulsed gradient is approximately along an axis of the borehole.

7. The method of claim 1, wherein generating the pulsed gradient field comprises:

pulsing at least one first gradient coil with a first current to produce a first gradient field; and pulsing at least one second gradient coil with a second current to produce a second gradient field that varies in a substantially different direction to the first gradient field.

8. The method of claim 1, further comprising:

using the phase encoded spin echo signals to form an image of the borehole.

9. A downhole NMR measurement device for use in a borehole, comprising:

at least one magnet to establish a magnetic field in a region of a formation that at least partially surrounds the measurement device;

at least one RF transmission coil to transmit RF, pulses pursuant to an NMR pulse sequence into the region to, in combination with the magnetic field, induce the generation of spin echo signals from a resonance volume within the region;

at least one gradient coil to generate a pulsed gradient field in the resonance volume; and circuitry coupled to said at least one gradient coil to control the generation of the pulsed gradient field to phase encode the spin echo signals, wherein the phase encoded spin echo signals are spatially located and are used to image in at least two dimensions at least one formation evaluation characteristic, independent of fluid flow within the formation, for a region of the formation that at least partially circumscribes the measurement device.

10. The NMR measurement apparatus of claim 9, wherein said at least one gradient coil comprises multiple gradient coils to establish a first gradient field component along a first direction and a second gradient field component along a second direction to combine with the first gradient field component to establish the gradient field in a direction of interest.

11. The NMR measurement apparatus of claim 10, wherein the multiple gradient coils comprises coil portions that are equally spaced about a longitudinal axis of the measurement apparatus and extend along the longitudinal axis near an outer surface of the magnet.

12. The NMR measurement apparatus of claim 10, wherein said at least one magnet has a first surface near a first end and a second surface near a second opposite end, a longitudinal axis of the measurement apparatus extending through the first and second surfaces;

the multiple gradient coils comprise first coil portions located near the first surface of said at least one magnet and second coil portions located near the second surface of said at least one magnet.

13. The NMR measurement apparatus of claim 12, wherein at least some of the first and second coil portions are arc-shaped.

14. The NMR measurement apparatus of claim 10, wherein said at least one magnet comprises a circularly cylindrical magnet polarized across its diameter.

15. The NMR measurement apparatus of claim 10, wherein said at least one magnet comprises a circularly cylindrical magnet polarized across its longitudinal axis.

16. The NMR measurement apparatus of claim 10, wherein said at least one magnet comprises a first magnet polarized in a first direction along a longitudinal axis of the NMR measurement apparatus and a second magnet polarized in a second opposite direction along the longitudinal axis; and the multiple gradient coils comprise a first gradient coil located between the first and second magnets to establish the first gradient component and a second gradient coil located between the first and second magnets to establish the second gradient component.

17. The NMR measurement apparatus of claim 9, wherein the gradient field varies with a longitudinal axis of the tool, said at least one gradient coil comprises:

a first set of gradient coils located near first surfaces of said at least one magnet to add to the magnetic field to create a positive gradient component of the gradient field; and a second set of gradient coils located near second surfaces of said at least one magnet to subtract from the magnetic field to create a negative gradient component of the gradient field.

18. The NMR measurement apparatus of claim 9, wherein the gradient field varies with a longitudinal axis of the tool, said at least one gradient coil comprises:

a first gradient coil located near a first end of said at least one magnet to add to the magnetic field to create a positive gradient component of the gradient field; and a second gradient coil located near a second end of said at least one magnet opposite from the first end to subtract from the magnetic field to create a negative gradient component of the gradient field.

19. The NMR measurement apparatus of claim 9, wherein the spin echo signals are localized to different parts of the region, the apparatus further comprising:

surface pads spaced around a longitudinal axis of the measurement apparatus and positioned near a wall of the borehole; and arrays of RF coils, each array attached to a different surface pad for measuring the spin echo signals localized to one of the parts of the region near the attached surface pad.

20. The NMR measurement apparatus of claim 19, wherein the RF coils of at least one of the arrays are arranged in rows and columns.

21. The NMR measurement apparatus of claim 19, wherein the circuitry is further adapted to use the arrays for purposes of tangential imaging of the formation about a longitudinal axis of the measurement apparatus.

22. The NMR measurement apparatus of claim 21, wherein the circuitry is further adapted to use a gradient field for the purpose of tangential imaging.

23. The NMR measurement apparatus of claim 21, wherein the circuitry is further adapted to not use a gradient field for the purpose of longitudinal imaging.

24. The NMR measurement apparatus of claim 19, wherein the circuitry is further adapted to use the array of coils as receivers and use at least one larger RF transmission coil.

25. The NMR measurement apparatus of claim 9, wherein the circuitry is further adapted to increase a magnitude of the gradient field.

26. The NMR measurement apparatus of claim 9, wherein the circuitry is further adapted to pulse said at least one gradient coil with a current between the reception of spin echo signals.

27. The NMR measurement apparatus of claim 9, wherein the NMR pulse sequence comprises successive refocusing pulses, each refocusing pulse producing a spin echo signal that precedes the next successive refocusing pulse in time; and the circuitry is further adapted to:

for every other spin echo signal, pulse at least one gradient coil with a current before said every other spin echo signal and after the last refocusing pulse and pulse said at least one gradient coil with the current after said every other spin echo signal and before the next refocusing pulse.

28. The NMR measurement apparatus of claim 9, wherein the circuitry is further adapted to vary the pulsed gradient field approximately tangentially around the borehole.

29. The NMR measurement apparatus of claim 9, wherein the circuitry is further adapted to vary the pulsed gradient field approximately along an axis of the borehole.

30. The NMR measurement apparatus of claim 9, wherein the circuitry is further adapted to:
   pulse at least one first gradient coil with a first current; and
   pulse at least one second gradient coil with a second current.

31. An NMR measurement device apparatus for use downhole comprising:
   at least one magnet to establish a magnetic field in a region of a formation that at least partially surrounds the measurement device;
   at least one RF transmission coil to transmit RF pulses pursuant to an NMR pulse sequence into the region to, in combination with the magnetic field, induce the generation of spin echo signals from a resonance volume within the region, the spin echo signals being localized to different parts of the region,
   surface pads spaced around a longitudinal axis of the measurement apparatus and positioned near a wall of the borehole; and
   arrays of RF receiving coils, each array attached to a different surface pad for measuring the spin echo signals localized to one of the parts of the region near the attached surface pad, wherein the spin echo signals are spatially located and are used to image in at least two-dimensions at least one formation evaluation characteristic, independent of fluid flow within the formation, for the region of the formation that at least partially circumscribes the measurement device.

32. The NMR measurement apparatus of claim 31, wherein the RF receiving coils of at least one of the arrays are arranged in rows and columns.

33. The NMR measurement apparatus of claim 31, wherein the circuitry is further adapted to use the arrays for purposes of tangential imaging of the formation about a longitudinal axis of the measurement apparatus.

34. The NMR measurement apparatus of claim 31, further comprising:
   circuitry adapted to use the RF coils as receiver antennas only; and
   at least one RF transmission coil.

35. A method usable with a downhole NMR measurement device apparatus, comprising:
   producing spin echo signals in a downhole formation;
   phase encoding the spin echo signals; and using the phase encoded spin echo signals to obtain at least a two-dimensional image of at least one formation evaluation characteristic, independent of fluid flow within the formation, of the downhole formation that circumscribes the measurement device.

36. The method of claim 35, wherein the image comprises a high resolution image.

37. The method of claim 35, wherein the producing comprises:
   using a magnet to polarize spins in a downhole formation that surrounds the NMR measurement apparatus; and
   transmitting RF pulses pursuant to an NMR pulse sequence into the downhole formation.

38. The method of claim 35, wherein the phase encoding the spin echo signals comprises:
   progressively increasing a magnitude of a pulsed gradient field.

39. The method of claim 35, wherein the phase encoding the spin echo signals comprises:
   pulsing at least one gradient coil with a current.

40. The method of claim 35, wherein
   producing the spin echo signals comprises transmitting an NMR pulse sequence,
   the NMR pulse sequence comprises successive refocusing pulses, each refocusing pulse producing a spin echo signal that precedes the next successive refocusing pulse in time; and
   the phase encoding the spin echo signals comprises:
      for every other spin echo signal, pulsing at least one gradient coil with a current before said every other spin echo signal and after the last refocusing pulse and pulsing said at least one gradient coil with the current after said every other spin echo signal and before the next refocusing pulse.

41. The method of claim 35, wherein the producing the phase encoded spin echo signals comprises:
   pulsing at least one first gradient coil with a first current to produce a first gradient field; and
   pulsing at least one second gradient coil with a second current to produce a second gradient field that varies in a substantially different direction to the first gradient field.

42. The method of claim 8 wherein the NMR measurement apparatus forms part of a drilling tool string and all of said method is performed while moving the drilling string along a wellbore traversing the downhole formation.

43. The method of claim 35 wherein the NMR measurement apparatus forms part of a drilling tool string and all of said method is performed while moving the drilling string along a wellbore traversing the downhole formation.

* * * * *